(12) United States Patent
Parthasaradhi Reddy et al.

(10) Patent No.: US 7,737,273 B2
(45) Date of Patent: Jun. 15, 2010

(54) PROCESS FOR ACYCLIC PHOSPHONATE NUCLEOTIDE ANALOGS

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN)

(73) Assignee: Hetero Drugs Limited, Hyderabad (IN)

( * ) Notice: Subject to any disclaimer, the term of this patent is extended or adjusted under 35 U.S.C. 154(b) by 44 days.

(21) Appl. No.: 11/572,054

(22) PCT Filed: Jul. 26, 2005

(86) PCT No.: PCT/IN2005/000247

§ 371 (c)(1),
(2), (4) Date: Sep. 24, 2008

(87) PCT Pub. No.: WO2007/013085

PCT Pub. Date: Feb. 1, 2007

(65) Prior Publication Data

US 2009/0012292 A1 Jan. 8, 2009

(51) Int. Cl.
*C07F 9/6561* (2006.01)
(52) U.S. Cl. .................................................. 544/244
(58) Field of Classification Search .................. 544/244
See application file for complete search history.

(56) References Cited

U.S. PATENT DOCUMENTS 4,808,716 A 2/1989 Hol et al.
5,922,695 A 7/1999 Arimilli et al.
5,977,061 A * 11/1999 Holy et al. .................... 514/7
6,069,249 A * 5/2000 Arimilli et al. .............. 544/243

FOREIGN PATENT DOCUMENTS

WO    WO 03/095665 A2   11/2003
WO    WO 2004/037161 A2   5/2004

OTHER PUBLICATIONS

Magdalenajidkova, Milena Masojfdkova and Ivan Rosenberg, Transprotection of N-Benzoylated Nucleobase Derivatives by Dialkylaminomethylene Group, Institute of Organic Chemistry and biochemistry, Academy of Sciences of the Czech Republic, Nucleotides & Nucleotides, 16(12), 2151-2164 (1997), pp. 2151-2164.
PCT Notification of Transmittal of the International Search Reort and the Written Opinion of the International Search Authority, International Application No. PCT/IN2005/000247.

* cited by examiner

*Primary Examiner*—Mark L Berch
(74) *Attorney, Agent, or Firm*—Caesar, Rivise, Bernstein, Cohen & Pokotilow, Ltd.

(57) ABSTRACT

The present invention provides a novel process for the preparation of acyclic phosphonate nucleotide analogs using novel intermediates. Thus, for example, (R)-9-(2-phosphonomethoxypropyl)adenine is reacted with dimethylformamide dimethylacetal to give $N^4$-dimethylaminomethyledino-9-(2-phosphonomethoxy ethyl) adenine, which is then reacted with chloromethyl-2-propyl carbonate in presence of triethylamine to give (R)-$N^4$-Dimethylaminomethyledino-9-(2-phosphono methoxypropyl) adenine disoproxil, followed by deprotection with acetic acid to get tenofovir disoproxil. Tenofovir disoproxil is then treated with fumaric acid to give tenofovir disoproxil fumarate.

42 Claims, No Drawings

PROCESS FOR ACYCLIC PHOSPHONATE NUCLEOTIDE ANALOGS

FIELD OF THE INVENTION

The present invention provides a novel process for the preparation of acyclic phosphonate nucleotide analogs using novel intermediates.

BACKGROUND OF THE INVENTION

Acyclic nucleoside phosphonates (ANPs) represent a class of nucleotide analogues in which a phosphonate group is linked to the alkyl side chain of various purines and pyrimidines. This class of nucleoside analogues possesses broad-spectrum antiviral activity, together with a high level of selectivity in vitro and in vivo. Among them adefovir chemically 9-(2-phosphonylmethoxyethyl)adenine and its ester derivatives (described in U.S. Pat. No. 4,808,716), tenofovir chemically (R)-9-(2-phosphonomethoxypropyl) adenine and its ester derivatives (described in U.S. Pat. No. 5,922,695) are having potent and selective activity against HIV and other retroviruses such as retro-, herpes- and hepadnaviruses.

Tenofovir disoproxil is represented by the following structure of formula 1:

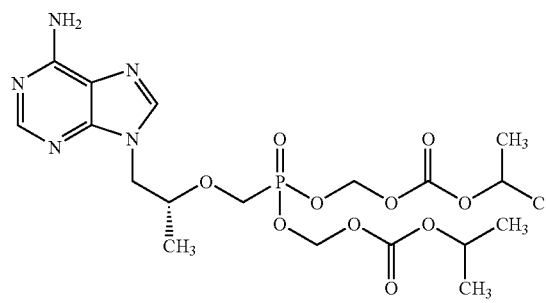

Adefovir dipivoxil is represented by the following structure of formula 2:

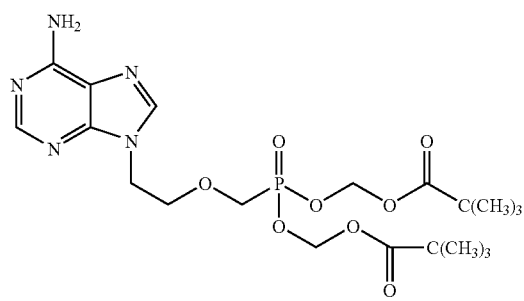

These compounds are normally prepared by the esterification of phosphonic acid of formula 3:

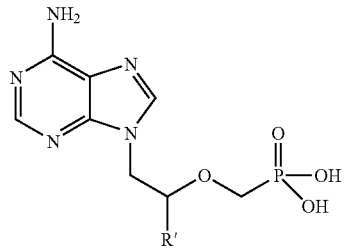

wherein R' is alkyl or H;

with an appropriate halide to obtain the compounds such as those shown in formula 2 and 3.

It has been found that introduction of groups such as isopropyloxycarbonyloxy methyl or pivaloyloxy methyl group to phosphonic acid compounds of formula 3 for the preparation of the phosphonic acid bis ester compounds such as tenofovir disoproxil of formula 1 or adefovir dipivoxil of formula 2 is associated with the problem of alkylation of $N^4$-amine group to form corresponding N-alkylated impurities. Excess use of alkylating agents leads to the formation of $N^4$-alkylated impurity. Similarly the use of lower quantities of alkylating agents leads to lower yields of products like tenofovir disoproxil and adefovir dipivoxil and formation of higher amounts of the corresponding mono ester impurities.

In an effort to solve the above said problems, we have succeeded in finding protecting agents that are advantageous in that a) the said protecting agents can successfully protect amino group and at the same time do not form esters with phosphonic acid group of the compound of formula I:

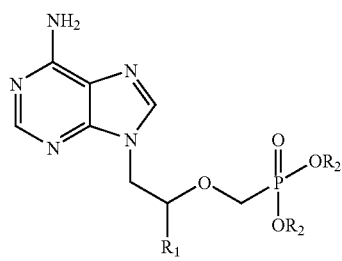

b) when the amine group is once protected with these protecting groups, then desired esterification can be carried out; and
c) then the said protecting group can be removed under conditions that does not hydrolyse or solvolyse the ester groups.

SUMMARY OF THE INVENTION

In accordance with the present invention, there is provided a process for preparing the compound of formula I:

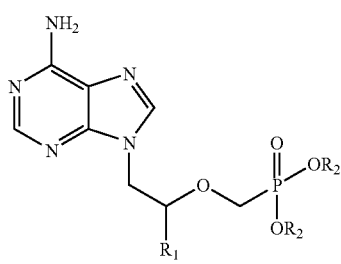

wherein $R_1$ is $C_1$ to $C_3$-alkyl or H; and $R_2$ is H or R—C(O)—OCH$_2$— wherein R is $C_1$ to $C_6$-alkyl or $C_1$ to $C_6$-alkoxide; provided both the $R_2$ are not H;

or a pharmaceutically acceptable salt thereof:

which comprises:

a) reacting the compound of formula II:

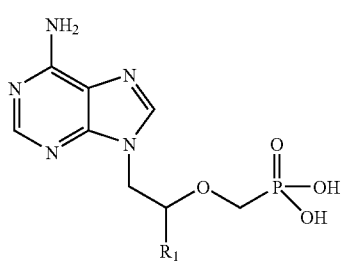

wherein $R_1$ is same as defined above with an acetal of formula III:

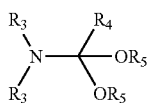

wherein $R_3$ is independently $C_1$ to $C_6$-alkyl or —H, wherein the said alkyl is unsubstituted or is substituted with 1 or 2 halo, cyano, nitro;

$R_4$ is H or $C_1$ to $C_6$-alkyl, wherein the said alkyl is unsubstituted or is substituted with 1 or 2 halo, cyano, nitro;

$R_5$ is $C_1$ to $C_6$-alkyl, wherein the said alkyl is unsubstituted or is substituted with 1 or 2 halo, cyano, nitro;

to obtain the compound of formula IV:

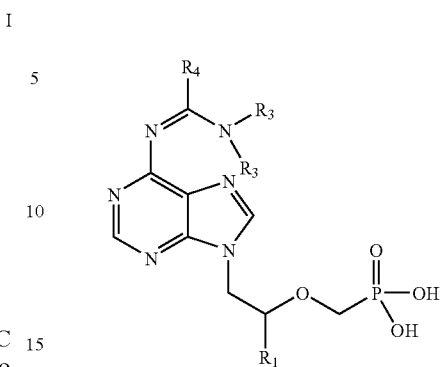

wherein $R_1$, $R_3$ and $R_4$ are same as defined above;

b) reacting the compound of formula IV with the compound of formula V:

$$R-C(O)-O-CH_2-Y \qquad V$$

wherein R is same as defined above, Y is a leaving group to form protected compound of formula VI:

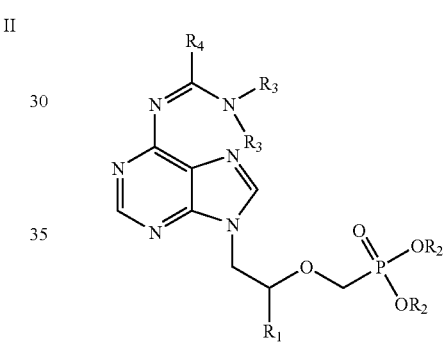

wherein $R_1$, $R_2$, $R_3$ and $R_4$ are same as defined above;

c) deprotecting the compound of formula VI to form the compound of formula I; and d) optionally converting the compound of formula I to a pharmaceutically acceptable salt.

The compounds of formula IV and VI are novel and form part of the invention.

DETAILED DESCRIPTION OF THE INVENTION

In accordance with the present invention, there is provided a process for preparing the compound of formula I:

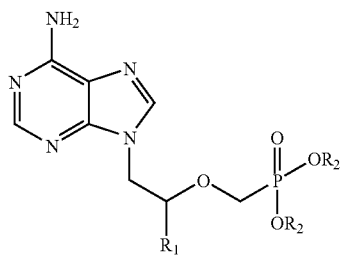

wherein $R_1$ is $C_1$ to $C_3$-alkyl or H; and $R_2$ is H or R—C(O)—OCH$_2$— wherein R is $C_1$ to $C_6$-alkyl or $C_1$ to $C_6$-alkoxide; provided both the $R_2$ are not H; or a pharmaceutically acceptable salt thereof using novel intermediates.

The process of the invention is described herein under.

The compound of formula II:

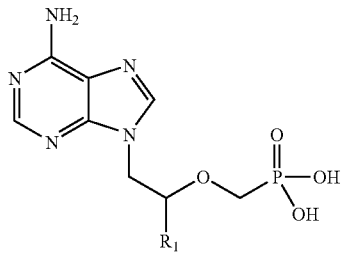

wherein $R_1$ is same as defined for formula I; is reacted with an acetal of formula III:

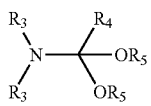

wherein $R_3$ is independently $C_1$ to $C_6$-alkyl or —H, wherein the said alkyl is unsubstituted or is substituted with 1 or 2 halo, cyano, nitro;

$R_4$ is H or $C_1$ to $C_6$-alkyl, wherein the said alkyl is unsubstituted or is substituted with 1 or 2 halo, cyano, nitro;

$R_5$ is $C_1$ to $C_6$-alkyl, wherein the said alkyl is unsubstituted or is substituted with 1 or 2 halo, cyano, nitro;

to obtain the compound of formula IV:

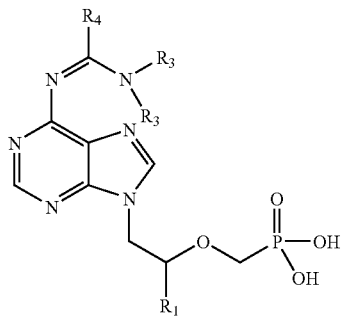

wherein $R_1$ is as defined for formula I; $R_3$ and $R_4$ are as defined for formula III.

The reaction of the compound of formula II with an acetal of formula III is carried out in any inert solvent. Preferably the reaction is carried out in N,N-dimethylformamide.

The reaction may be carried out at below the boiling temperature of the solvent used, preferably at 20° C. to boiling temperature of the solvent used.

The compound of formula IV obtained above can be used directly in the next step; or can be isolated from the reaction mass and then used in the next step.

The compound of formula IV is reacted with the compound of formula V:

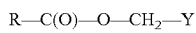

wherein R is same as defined for formula I, Y is a leaving group to obtain protected compound of formula VI:

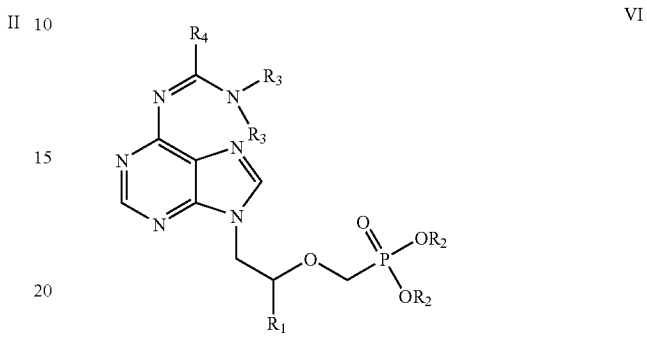

wherein $R_1$ and $R_2$ are as defined for formula I, and $R_3$ and $R_4$ are as defined for formula III.

Preferably R is isopropoxy- or tert-butyl, and the leaving group Y is halo or sulfonyloxy. Preferable halo group is chloro or bromo and more preferable halo group is chloro.

Preferably the sulfonyloxy group is methane sulfonyloxy, benzene sulfonyloxy, o, m or p-toluene sulfonyloxy or m-nitrobenzene sulfonyloxy group.

Preferably both the $R_2$ groups are R—C(O)—OCH$_2$—.

Preferably, more than two moles of the compounds of formula V are used per mole of the compounds of formula IV to obtain the compound VI, wherein both the $R_2$ groups are R—C(O)—OCH$_2$—, more preferably, 3 to 15 moles, still more preferably 3 to 10 moles of the compounds of formula V are used per mole of the compound of formula IV.

The reaction may be carried out in any suitable solvent and may be carried out at 10° C. to boiling temperature of the solvent used. Preferable solvent is selected from ester solvents such as ethyl acetate, methyl acetate, isopropyl acetate, tert-butyl acetate, ethyl formate and methyl formate; N,N-dimethyl formamide; N,N-dimethylacetamide; dimethyl sulfoxide; cyclic amide solvents such as N-methyl-2-pyrrolidinone; dioxane; tetrahydrofuran; ketonic solvents such as acetone, diethyl ketone, methyl ethyl ketone, methyl isobutyl ketone and methyl propyl ketone; chlorinated hydrocarbon solvents such as methylene chloride, chloroform, carbon tetrachloride and ethylene dichloride; hydrocarbon solvents such as benzene, toluene, xylene, hexane and cyclohexane; and ether solvents such as diethyl ether, diisopropyl ether and tert-butyl methyl ether. More preferable solvent is selected from N-methyl-2-pyrrolidinone, N,N-dimethylformamide, N,N-dimethylacetamide and tetrahydrofuran. Most preferable solvent is N-methyl-2-pyrrolidinone or N,N-dimethylformamide.

The reaction is preferably carried out in the presence of a base such as an amine base.

The compound of formula VI may preferably be crystallized from the reaction mass or the compound of formula VI may be used directly in the next step.

The compound of formula VI is subjected to deprotection to obtain the compound of formula I.

The deprotection may be carried out using for example carboxylic acids such as formic acid, acetic acid or sulfonic acids such as methane sulfonic acid, toluene sulfonic acid, water or a mixture thereof. The reagent used for deprotection is not critical so far as phosphonic ester group is not hydrolysed or solvolysed.

The compound of formula I is optionally converted to the pharmaceutically acceptable salts by known methods.

$R_3$ in the formulae III and IV are preferably independently $C_1$ to $C_6$-alkyl, more preferably methyl or ethyl and still more preferably methyl.

$R_4$ in the formulae III, IV and VI are preferably —H.

$R_5$ in the formula III is preferably methyl or ethyl.

$R_1$ in the formulae I, II, IV and VI are preferably methyl or H.

If $R_1$ is alkyl, the compound of formula II, IV, VI and I are represent enantiomers and mixture of enantiomers and come under the scope of the invention.

The preferred compounds of formula I prepared according to the present invention are the compounds of formula I wherein R is isopropoxy or tert-butyl and $R_1$ is H or methyl. Preferable compounds of formula I are i) (R)-9-(2-phosphonomethoxypropyl) adenine bis(isopropyloxycarbonyloxy methyl) ester (tenofovir disoproxil) and ii) 9-(2-phosphonylmethoxyethyl)adenine di(pivaloyloxymethyl) ester (adefovir dipivoxil).

The preferred compounds of formula IV are the compounds of formula IV wherein $R_1$ is methyl or H; $R_3$ is methyl or ethyl, and $R_4$ is H.

Preferable compounds of formula VI are the compounds of formula VI wherein $R_3$ is methyl or ethyl, $R_4$ is H; $R_1$ is H or methyl and R is isopropoxy or tert-butyl.

The invention will now be further described by the following examples, which is illustrative rather than limiting.

Example 1

Step-I (R)-9-(2-phosphonomethoxypropyl)adenine (14 gm) is dissolved in dimethylformamide (60 ml) and dimethylformamide dimethylacetal (21 gm) is added slowly at 25-30° C. for 10 minutes. The temperature is raised to 55° C. and maintained for 3 hours at 50-55° C. Then the solvent is distilled under vacuum at 75-80° C. to give 20 gm of (R)-$N^4$-Dimethylaminomethyledino-9-(2-phosphonomethoxypropyl)adenine as residue.

Step-II

To the mixture of (R)-$N^4$-Dimethylaminomethyledino-9-(2-phosphono methoxypropyl)adenine (20 gm), N-methyl-2-pyrrolidinone (80 ml) and triethyl amine (20 ml), chloromethyl-2-propyl carbonate (30 gm) is added slowly at 25-30° C. for 30 minutes, the temperature is raised to 60° C. and maintained for 4 hours at 55-60° C. Then the reaction mass is cooled to 25-30° C. Ethyl acetate (260 ml) is added and stirred for 20 minutes at 25-30° C. Filtered the salts on hi-flo bed and washed the ethyl acetate layer with water (140 ml), then washed with 10% sodium chloride (100 ml) and then the resulting organic layer is distilled under vacuum to give 20 gm of (R)-$N^4$-Dimethylaminomethyledino-9-(2-phosphono methoxypropyl) adenine bis(isopropyloxycarbonyloxymethyl) ester.

Step-III (R)-$N^4$-Dimethylaminomethyledino-9-(2-phosphonomethoxypropyl) adenine bis(isopropyloxycarbonyloxymethyl) ester (10 gm) is added to 80% acetic acid (80 ml) at 25-30° C., the temperature is raised to 50-55° C. and maintained for 3 hours at the same temperature. Then acetic acid is distilled under vacuum at 70° C. Water (40 ml) and ethyl acetate (130 ml) are added to the residue, pH of the solution is adjusted to 7.0 with triethylamine and then separated the layers. The resulting organic layer is washed with 10% sodium chloride solution (35 ml) and distilled under a vacuum to give 8 gm of tenofovir disoproxil (HPLC Purity: 99.2%).

Step-IV

Tenofovir disoproxil (2.5 gm) is dissolved in isopropyl alcohol (12.5 ml), fumaric acid (0.6 gm) is added at 25-30° C. and then the temperature is raised to 45° C., maintained for 20 minutes. The reaction mass is cooled to 25-30° C. and stirred for 1 hour at the same temperature and again mass is cooled to 0-5° C., stirred for 1 hour at 0-5° C. Filtered the material, washed with isopropyl alcohol (2 ml) and finally washed with hexane to give 2.4 gm of tenofovir disoproxil fumarate (HPLC Purity: 99.8%).

Example 2

Step-I 9-(2-Phosphonomethoxyethyl)adenine (20 gm) is dissolved in dimethyl formamide (80 ml) and dimethylformamide dimethylacetal (30 gm) is added slowly at 25-30° C. for 10 minutes. The temperature is raised to 55° C. and maintained for 3 hours at 50-55° C. Then the solvent is distilled under vacuum at 75-80° C. to give 28 gm of $N^4$-dimethylaminomethyledino-9-(2-phosphono methoxyethyl) adenine as residue.

Step-II

To the mixture of $N^4$-dimethylaminomethyledino-9-(2-phosphonomethoxy ethyl) adenine (25 gm), N-methyl-2-pyrrolidinone (100 ml) and triethylamine (38 gm), chloromethyl pivalate (57 gm) is added slowly at 25-30° C. for 30 minutes, the temperature is raised to 45° C. and maintained for 19 hours at 40-45° C. Then the reaction mass is cooled to 25-30° C. and filtered the salts on hi-flo bed. To the reaction mass ethyl acetate (300 ml) is added and stirred for 20 minutes at 25-30° C. The ethyl acetate layer is washed with water (175 ml) and then washed with 10% sodium chloride solution (125 ml). The resulting organic layer is distilled under vacuum to give 30 gm of $N^4$-dimethylaminomethyledino-9-(2-phosphonomethoxy ethyl)adinine di(pivaloyloxymethyl) ester.

Step-III $N^4$-Dimethylaminomethyledino-9-(2-phosphonomethoxy ethyl) adinine di(pivaloyloxymethyl) ester (10.5 gm) is added to 80% acetic acid (80 ml) at 25-30° C., the temperature is raised to 50-55° C. and maintained for 3 hours at the same temperature. Then acetic acid is distilled under vacuum at 70° C. Water (50 ml) and ethyl acetate (150 ml) are added to the residue, pH of the solution is adjusted to 7.5 with triethylamine and then separated the layers. The resulting organic layer is washed with 10% sodium chloride solution (50 ml), distilled under vacuum and the residue obtained is crystallized from acetone/diisopropyl ether to give 8 gm of adefovir dipivoxil (HPLC Purity: 99.6%).

We claim:

1. A process for preparation of the compound of formula I:

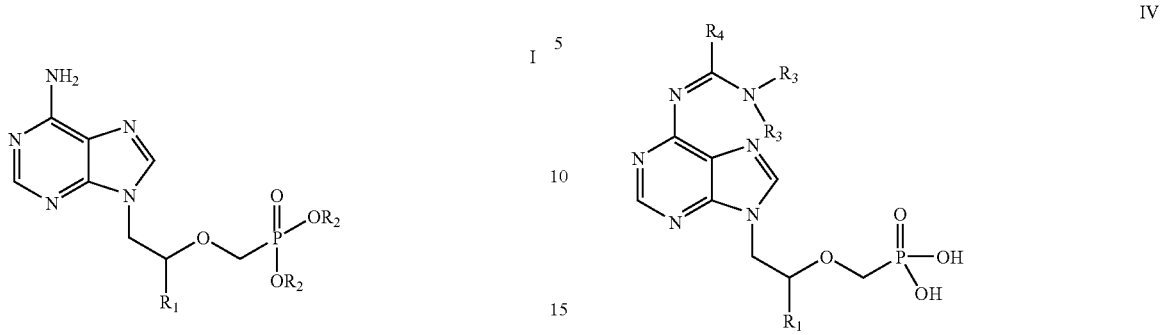

wherein $R_1$ is $C_1$ to $C_3$-alkyl or H; and $R_2$ is H or R—C(O)—OCH$_2$— wherein R is $C_1$ to $C_6$-alkyl or $C_1$ to $C_6$-alkoxide; provided both the $R_2$ are not H;

or a pharmaceutically acceptable salt thereof:

which comprises:

a) reacting the compound of formula II:

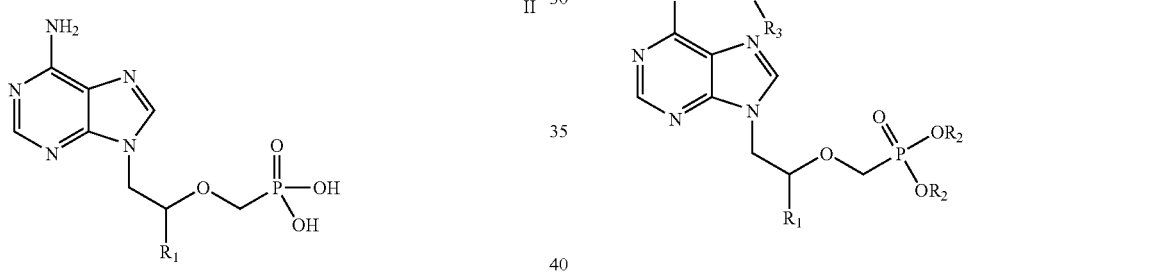

wherein $R_1$ is same as defined above with an acetal of formula III:

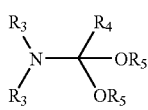

wherein $R_3$ is independently $C_1$ to $C_6$-alkyl or H, wherein the said alkyl is unsubstituted or is substituted with 1 or 2 halo, cyano, nitro;

$R_4$ is H or $C_1$ to $C_6$-alkyl, wherein the said alkyl is unsubstituted or is substituted with 1 or 2 halo, cyano, nitro;

$R_5$ is $C_1$ to $C_6$-alkyl, wherein the said alkyl is unsubstituted or is substituted with 1 or 2 halo, cyano, nitro;

to obtain the compound of formula IV:

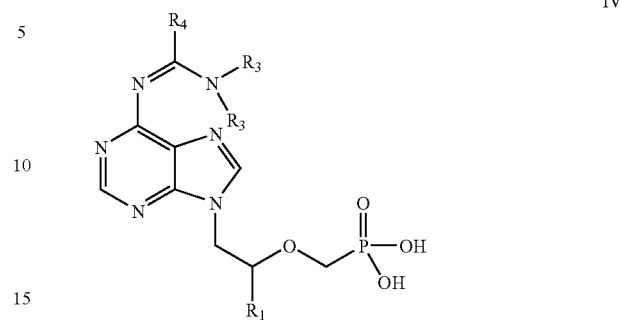

wherein $R_1$, $R_3$ and $R_4$ are same as defined above;

b) reacting the compound of formula IV with the compound of formula V:

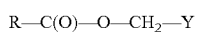

R—C(O)—O—CH$_2$—Y        V wherein R is same as defined above, Y is a leaving group to form protected compound of formula VI:

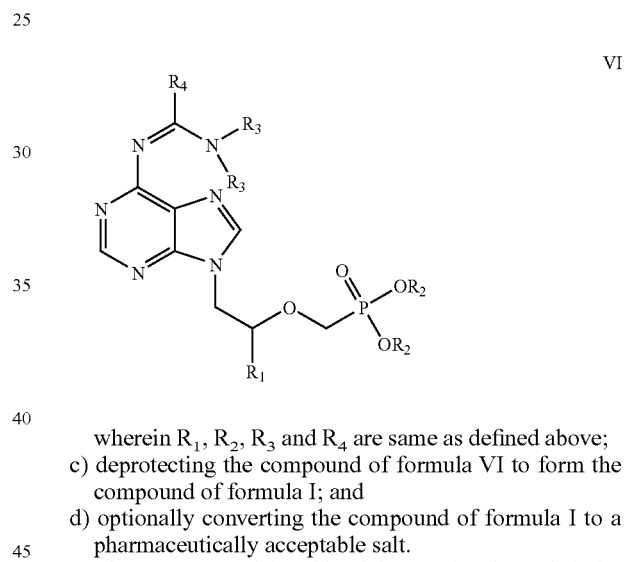

wherein $R_1$, $R_2$, $R_3$ and $R_4$ are same as defined above;

c) deprotecting the compound of formula VI to form the compound of formula I; and d) optionally converting the compound of formula I to a pharmaceutically acceptable salt.

2. The process as claimed in claim 1, wherein $R_3$ is independently $C_1$ to $C_6$-alkyl.

3. The process as claimed in claim 2, wherein $R_3$ is methyl or ethyl.

4. The process as claimed in claim 3, wherein $R_3$ is methyl.

5. The process as claimed in claim 1, wherein $R_4$ is H; $R_5$ is methyl or ethyl and $R_1$ is methyl or H.

6. The process as claimed in claim 5, wherein $R_5$ is methyl and $R_1$ is methyl.

7. The process as claimed in claim 1, wherein the reaction in step (a) is carried out in an inert solvent.

8. The process as claimed in claim 7, wherein the solvent is N,N-dimethyl formamide.

9. The process as claimed in claim 1, wherein the reaction in step (a) is carried out at below the boiling temperature of the solvent used.

10. The process as claimed in claim 9, wherein the reaction is carried out at 20° C. to boiling temperature of the solvent used.

11. The process as claimed in claim 1, wherein the R in formula V is isopropoxy- or tert-butyl, and the leaving group Y is halo or sulfonyloxy, wherein the sulfonyloxy group is methane sulfonyloxy, benzene sulfonyloxy, o, m or p-toluene sulfonyloxy or m-nitrobenzene sulfonyloxy group.

12. The process as claimed in claim 11, wherein the halo group is chloro or bromo.

13. The process as claimed in claim 12, wherein the halo group is chloro.

14. The process as claimed in claim 1, wherein both the $R_2$ groups in formula VI are R—C(O)—OCH$_2$—.

15. The process as claimed in claim 1, wherein the reaction in step (b), more than two moles of the compounds of formula V are used per mole of the compounds of formula IV to obtain the compound VI.

16. The process as claimed in claim 15, wherein 3 to 15 moles of the compounds of formula V are used per mole of the compounds of formula IV.

17. The process as claimed in claim 16, wherein 3 to 10 moles of the compounds of formula V are used per mole of the compounds of formula IV.

18. The process as claimed in claim 1, wherein the reaction in step (b) is carried out in a suitable solvent and is carried out at 10° C. to boiling temperature of the solvent used.

19. The process as claimed in claim 18, wherein the solvent is selected from ester solvents; N,N-dimethylformamide; N,N-dimethylacetamide; dimethyl sulfoxide; cyclic amide solvents; dioxane; tetrahydrofuran; ketonic solvents; chlorinated hydrocarbon solvents; hydrocarbon solvents; and ether solvents.

20. The process as claimed in claim 19, wherein the solvent is selected from N-methyl-2-pyrrolidinone, N,N-dimethylformamide, N,N-dimethylacetamide and tetrahydrofuran.

21. The process as claimed in claim 19, wherein the solvent is N-methyl-2-pyrrolidinone or N,N-dimethylformamide.

22. The process as claimed in claim 1, wherein the reaction in step (b) is carried out in presence of a base.

23. The process as claimed in claim 22, wherein the base is an amine base.

24. The process as claimed in claim 1, wherein the deprotection in step (c) is carried out using carboxylic acids or sulfonic acids, water or a mixture thereof.

25. The process as claimed in claim 1, wherein the compounds of formula I prepared are the compounds of formula I wherein R is isopropoxy or tert-butyl and $R_1$ is H or methyl.

26. The process as claimed in claim 25, wherein the compound of formula 1 is
i) (R)-9-(2-phosphonomethoxypropyl) adenine bis(isopropyloxycarbonyloxy methyl) ester (tenofovir disoproxil) or
ii) 9-(2-phosphonylmethoxyethyl)adenine di(pivaloyloxymethyl) ester (adefovir dipivoxil).

27. Compound of formula IV:

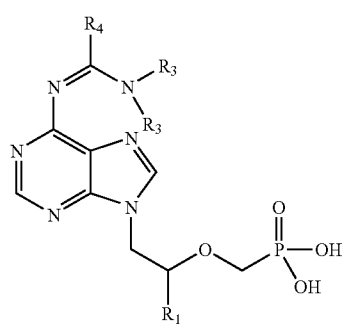

wherein $R_1$ is $C_1$ to $C_3$-alkyl or H; $R_3$ is independently $C_1$ to $C_6$-alkyl or —H, wherein the said alkyl is unsubstituted or is substituted with 1 or 2 halo, cyano, nitro; and $R_4$ is H or $C_1$ to $C_6$-alkyl, wherein the said alkyl is unsubstituted or is substituted with 1 or 2 halo, cyano, nitro.

28. The compound as claimed in claim 27, wherein $R_1$ is methyl or H; $R_3$ is methyl or ethyl; and $R_4$ is H.

29. (R)-N$^4$-Dimethylaminomethyledino-9-(2-phosphonomethoxypropyl) adenine.

30. N$^4$-dimethylaminomethyledino-9-(2-phosphonomethoxyethyl) adenine.

31. Compound of formula VI:

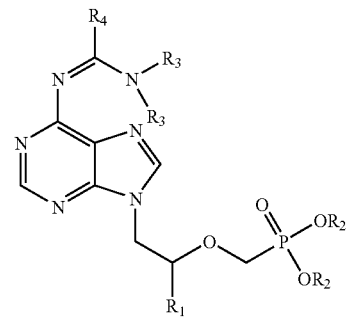

wherein $R_1$ is $C_1$ to $C_3$-alkyl or H; $R_2$ is H or R—C(O)—OCH$_2$— wherein R is $C_1$ to $C_6$-alkyl or $C_1$ to $C_6$-alkoxide; provided both the $R_2$ are not H; $R_3$ is independently $C_1$ to $C_6$-alkyl or —H, wherein the said alkyl is unsubstituted or is substituted with 1 or 2 halo, cyano, nitro; and $R_4$ is H or $C_1$ to $C_o$-alkyl, wherein the said alkyl is unsubstituted or is substituted with 1 or 2 halo, cyano, nitro.

32. The compound as claimed in claim 30, wherein $R_3$ is methyl or ethyl, $R_4$ is H, $R_1$ is H or methyl and R is isopropoxy or tert-butyl.

33. (R)-N$^4$-Dimethylaminomethyledino-9-(2-phosphonomethoxypropyl)adenine bis(isopropyloxycarbonyloxymethyl) ester.

34. N$^4$-dimethylaminomethyledino-9-(2-phosphonomethoxyethyl)adinine di(pivaloyloxymethyl) ester.

35. The process as claimed in claim 19, wherein the ester solvent is selected from the group consisting of ethyl acetate, methyl acetate, isopropyl acetate, tert-butyl acetate ethyl formate, and methyl formate.

36. The process as claimed in claim 19, wherein the cyclic amide solvent is N-methyl-2-pyrrolidinone.

37. The process as claimed in claim 19, wherein the ketonic solvent is selected from the group consisting of acetone, diethyl ketone, methyl ethyl ketone, methyl isobutyl ketone, and methyl propyl ketone.

38. The process as claimed in claim 19, wherein the chlorinated hydrocarbon solvent is selected from the group consisting of methylene chloride, chloroform, carbon tetrachloride, and ethylene dichloride.

39. The process as claimed in claim 19, wherein the hydrocarbon solvent is selected from the group consisting of benzene, toluene, xylene, hexane, and cyclohexane.

40. The process as claimed in claim 19, wherein the ether solvent is selected from the group consisting of diethyl ether, diisopropyl ether, and tert-butyl methyl ether.

41. The process as claimed in claim 24, wherein the carboxylic acid is selected from the group consisting of formic acid, and acetic acid.

42. The process as claimed in claim 24, wherein the sulfonic acid is selected from the group consisting of methane sulfonic acid, and toluene sulfonic acid.

* * * * *